United States Patent
Tien et al.

(10) Patent No.: US 9,115,160 B2
(45) Date of Patent: Aug. 25, 2015

(54) SOLVENT-FREE PROCESS FOR THE PREPARATION OF CYCLOPHOSPHAMIDE

(71) Applicant: Sunny Pharmtech Inc., Taoyuan County (TW)

(72) Inventors: Jien-Heh Tien, Taoyuan County (TW); Pi-Shan Chiang, Changhua (TW)

(73) Assignee: SUNNY PHARMTECH INC., Taoyuan County (TW)

( * ) Notice: Subject to any disclaimer, the term of this patent is extended or adjusted under 35 U.S.C. 154(b) by 0 days.

(21) Appl. No.: 14/013,211

(22) Filed: Aug. 29, 2013

(65) Prior Publication Data

US 2014/0066654 A1    Mar. 6, 2014

Related U.S. Application Data

(60) Provisional application No. 61/695,530, filed on Aug. 31, 2012.

(51) Int. Cl.
*C07F 9/6584* (2006.01)

(52) U.S. Cl.
CPC .................. *C07F 9/65846* (2013.01)

(58) Field of Classification Search
CPC .................................................. C07F 9/65846
USPC ............................................................ 564/13
See application file for complete search history.

(56) References Cited

U.S. PATENT DOCUMENTS 5,616,789 A * 4/1997 South et al. ................... 562/439
2001/0047103 A1 * 11/2001 Niemeyer et al. ............... 558/81

FOREIGN PATENT DOCUMENTS

WO    WO99/55857    * 11/1999

OTHER PUBLICATIONS

Kumar et al., "Synthesis and Biological Evaluation of Some Cyclic Phosphoramidate Nucleoside Derivatives," J. Med. Chem., 33(9), 1990, 2368-2375.*
Bezgubenko et al., "Phosphorus Halides Complexes with 4-Dimethylaminopyridine and N-Methylimidazole," Russian Journal of General Chemistry, 2009, 79(5), 911-918.*
D'Anna, Kemp Elimination: A Probe Reaction to Study Ionic Liquids Properties, J. Org. Chem. 2008, 73, 3397-3403.*

* cited by examiner

*Primary Examiner* — Paul A Zucker
*Assistant Examiner* — Mark Luderer
(74) *Attorney, Agent, or Firm* — WPAT, PC; Justin King

(57) ABSTRACT

This invention discloses a solvent-free process for the preparation of cyclophosphamide. According to this invention, there is no solvent used during the reaction step for preparing cyclophosphamide, so that the total volume of the reaction for preparing cyclophosphamide can be reduced and the manufacture of cyclophosphamide can become more efficient. Furthermore, the above solvent-free process for the preparation of cyclophosphamide is more simply operated, more economic, and more environmental friendly than the preparation of cyclophosphamide in the prior art.

10 Claims, No Drawings

SOLVENT-FREE PROCESS FOR THE PREPARATION OF CYCLOPHOSPHAMIDE

BACKGROUND OF THE INVENTION

1. Field of the Invention

The present invention is generally related to a process for the preparation of cyclophosphamide, and more particularly to a solvent-free process for the preparation of cyclophosphamide.

2. Description of the Prior Art

In recent years, it is well known that cyclophosphamide and its derivatives have cytostatic and immunosuppressant's activity. Cyclophosphamide presents a high potent character as an anti-cancer/anti-tumor drug. During the preparation of cyclophosphamide, it is essential to have high purity of the product and also the conversion yield of the synthesis.

In literature, all the procedures of preparing cyclophosphamide required an inert organic solvent or solvent mixtures. The solvent(s) used are not parts of constitution of the molecule and it will increase the total volume of the reaction for preparing cyclophosphamide which will decrease the volume efficiency. Cyclophosphamide is a high potency drug, and it has high bioactivity in human body with a very small dosage. Therefore, it is very important to protect the operator(s) during the manufacturing of high potency drug and controls the environment of production facilities. Generally speaking, high potency drug such as cyclophosphamide is produced with small volume reaction reactors due to the control and safety concerns. When the used solvent occupies most volume of the reaction tanks, the manufacturing efficiency will be decreased and the batch efficiency for the preparation of cyclophosphamide will decrease. The manufacturing cost will increase as the result of poor throughputs. And it is also true that the solvents used in the reaction will let the operator(s) expose in volatile organic solvent(s) which may contain trace amount of cyclophosphamide because of its low vapor pressure property of cyclophosphamide. This will present a hazard-working environment for the operators.

It is well disclosed in literature that it is important to control the amount of water in the reaction mixture for the preparation of cyclophosphamide. While the amount of water is increased during preparing cyclophosphamide, the amount of by-product(s) will be increased and the total conversion yield will be decreased. The solvents used in the reaction are the major source of the water that needed be controlled. When large amount of solvents are used, it absolutely need to decrease the water content of solvent by either distillation under anhydrous conditions before use or by other means such as using dehydrate reagents during the reaction. Molecular sieves and $CaCl_2$ are commonly added into the reaction mixture to remove water as part of the preparing procedures.

In the prior literature, dichloromethane or dioxane can be used as solvent for preparing cyclophosphamide. It is well known that the water contained in dioxane is hard to be removed and the by-products will increase as the results of high water contents in the reaction. Dioxane is a toxic solvent and it is not only dangerous to the operator(s) but also bring an added-cost to prevent pollution after the reaction.

From the discussion as stated, to develop a novel solvent-free process for the preparation of cyclophosphamide is important. It offers the advantages of high conversion rate, high throughputs and easy environmental and operation control with great cost benefits.

SUMMARY OF THE INVENTION

In light of the above background, in order to fulfill the requirements of the industry, the present invention provides a novel solvent-free process for the preparation of cyclophosphamide having the advantages of high conversion yield, high product purity, more easy operation, and environmental friendly with great manufacturing cost benefits.

One object of the present invention is to provide a solvent-free process for the preparation of cyclophosphamide to be more environmental friendly by employing no solvent during the reaction of cyclophosphamide to decrease chemical waste.

Another object of the present invention is to provide a solvent-free process for the preparation of cyclophosphamide to improve the total conversion yield, and purity of the cyclophosphamide product by performing two-stage one-pot operation without isolating the intermediate thereof.

Still another object of the present invention is to provide a solvent-free process for the preparation of cyclophosphamide to simplify the operation of the preparation of cyclophosphamide and the preparatory works before the reaction by performing a solvent-free process without considering the water contained in solvent(s) or drying solvent(s) before use.

Accordingly, the present invention discloses a solvent-free process for the preparation of cyclophosphamide. The mentioned solvent-free process for the preparation of cyclophosphamide comprises reacting phosphoryl chloride, bis(2-chloroethyl)amine hydrochloride, 3-aminopropanol and base for producing cyclophosphamide. According to this invention, there could be no solvent used in the reaction for producing cyclophosphamide.

In one embodiment of this invention, said phosphoryl chloride is employed to react with said bis(2-chloroethyl)amine hydrochloride in the environment with said base to produce a first intermediate. The first intermediate is subsequently employed to react with said 3-aminopropanol to obtain cyclophosphamide.

In one embodiment, said base can be selected from one or any combination of the group consisted of the following: N-alkylmorpholine, N,N'-Dialkylpiperazine.

In one embodiment, said bis(2-chloroethyl)amine hydrochloride can be mixed with said base and heated to raise the reactivity of said bis(2-chloroethyl)amine hydrochloride.

In one embodiment, the solvent-free process for the preparation of cyclophosphamide can further comprise a step of adding catalyst into the first stage of the two-stage one-pot operation. Said catalyst can be selected from one or any combination of the group consisted of the following: N-hydroxysuccinimide (HOSu), hydroxybenzotriazole (HOBt), 4-Dimethylaminopyridine (DMAP).

In one embodiment, the mentioned solvent-free process for the preparation of cyclophosphamide can react said 3-aminopropanol with said phosphoryl chloride in the environment with said base to produce a second intermediate. And, the second intermediate is subsequently employed to react with said bis(2-chloroethyl)amine hydrochloride to obtain cyclophosphamide.

To sum up, this invention discloses a solvent-free process for the preparation of cyclophosphamide. The mentioned preparation can be performed through the reaction without any solvent. Preferably, the mentioned preparation is a two-stage one-pot operation without isolating the intermediate thereof, and the total conversion yield and product purity of the preparation can be efficiently improved. Because of using no solvent in the reaction, the total volume of the reaction can be reduced, and the product yield of each batch can be improved. Therefore, the batch number of producing the cyclophosphamide and the manufacturing cost can be decreased. Moreover, cyclophosphamide is a high potency drug, and it is usually employed in a small-scale reaction tank to manufacture cyclophosphamide, so that it is convenient to control the manufacturing safety and the product quality. For high potency drug as cyclophosphamide, to improve manufacturing efficiency is important in research and is with high industrial value.

DESCRIPTION OF THE PREFERRED EMBODIMENTS

What probed into the invention is a solvent-free process for the preparation of cyclophosphamide. Detailed descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

One preferred embodiment according to this specification discloses a solvent-free process for the preparation of cyclophosphamide. According to this embodiment, the mentioned solvent-free process comprises reacting a phosphoryl halide, an amine hydrohalide salt, a hydroxyl amine, and a base. The general formula of the mentioned phosphoryl halide, amine hydrohalide salt, hydroxyl amine, and cyclophosphamide are as following:

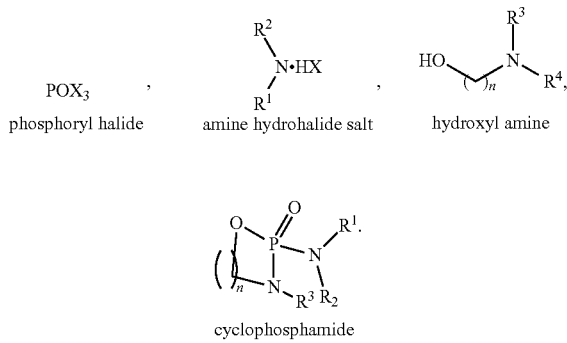

In the above-mentioned formula, X is selected from Cl, Br. $R^1$, $R^2$, and $R^3$ can be identical or different, and are independently selected from the group consisting of the following: C1-C6 alkyl group, C1-C6 cycloalkyl group, C2-C6 alkoxy group, halogen substituted C1-C6 alkyl group, C1-C6 acyl group, C6-C12 aryl group, C6-C12 conjugated aromatic group, C6-C12 heterocyclic aromatic group, C3-C6 cycloalkenyl group. $R^4$ is H atom. n is 3. In one preferred example of this embodiment, the mentioned amine is a salt with hydrohalide, such as hydrochloride, hydrobromide.

In one preferred example of this embodiment, said base can be selected from one or any combination of the group consisting of the following:

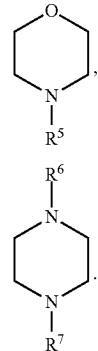

In the above-mentioned formula, $R^5$, $R^6$, and $R^7$ can be identical or different, and are independently selected from the group consisting of the following: C1-C3 straight-chain alkyl group, C1-C3 branched alkyl group.

In one preferred example of this embodiment, the mentioned base is about 5-12 equivalent.

According to this embodiment, the mentioned solvent-free process for the preparation of cyclophosphamide can be shown as following Scheme 1.

Scheme 1

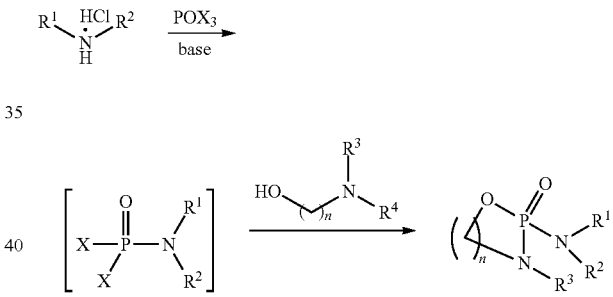

According to this embodiment, referred to Scheme 1, the mentioned phosphoryl halide is reacted with the amine hydrohalide salt in the environment with the base in the first stage, and an intermediate is produced. The mentioned intermediate, without isolated, is subsequently reacted with the hydroxyl amine in the second stage as shown in Scheme 1, and the cyclophosphamide is obtained. The mentioned preparation is performed as two-stage one-pot operation.

Another preferred embodiment according to this specification discloses a solvent-free process for the preparation of cyclophosphamide. The mentioned solvent-free process comprises reacting phosphoryl chloride, bis(2-chloroethyl) amine hydrochloride, 3-aminopropanol, and base. The general formula of the mentioned phosphoryl chloride, bis(2-chloroethyl)amine hydrochloride, 3-aminopropanol, base, and cyclophosphamide are as following:

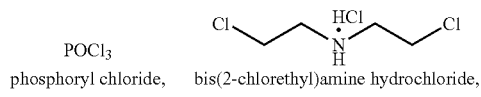

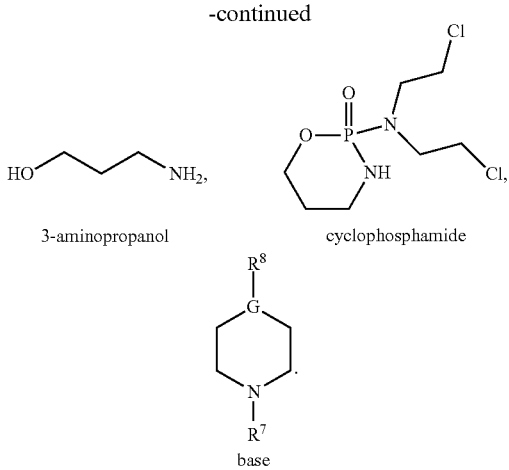

In the above-mentioned formula, G is selected from one of the following: N, O. $R^7$ can be selected from the group consisting of the following: C1-C3 straight-chain alkyl group, C1-C3 branched alkyl group. When G is N, $R^8$ can be selected from the group consisting of the following: C1-C3 straight-chain alkyl group, C1-C3 branched alkyl group.

In one preferred example of this embodiment, the amount of the mentioned base used in the solvent-free process is about 5-12 equivalent. The mentioned base is selected from one or any combination of the group consisted of the following: N-methyl morpholine, N,N-dimethylpiperazine.

In one preferred example of this embodiment, the solvent-free process for the preparation of cyclophosphamide can be presented as following Scheme 2.

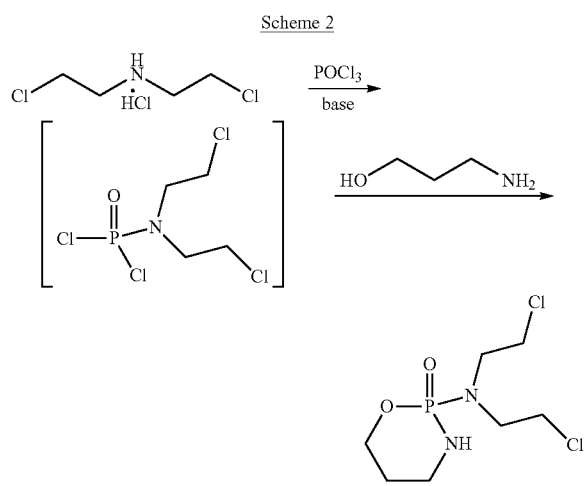

As presented in the above Scheme 2, bis(2-chloroethyl)amine hydrochloride can react with phosphoryl chloride ($POCl_3$) in the environment with the mentioned base to produce the first intermediate in the first stage of the solvent-free process. The mentioned first intermediate is subsequently reacted with 3-aminopropanol to obtain cyclophosphamide in the second stage of the above solvent-free process, wherein the first intermediate does not pass through isolation before reacting with 3-aminopropanol. The solvent-free process of this presented example can be performed as 2-stage one-pot operation.

The reaction of bis(2-chloroethyl)amine hydrochloride and $POCl_3$ is an exothermic reaction. Therefore, in one preferred example of this embodiment, $POCl_3$ is slowly dropped into bis(2-chloroethyl)amine hydrochloride with the base with ice-bathed condition. In one preferred example of this embodiment, the temperature of the mentioned first stage reaction is controlled at about −10 to 50° C.

In one preferred example of this embodiment, the base can be added into the bis(2-chloroethyl)amine hydrochloride at the beginning. In another preferred example of this embodiment, in order to improve the reactivity of the bis(2-chloroethyl)amine hydrochloride and make the reaction between the bis(2-chloroethyl)amine hydrochloride and the base more completely, the mentioned first stage reaction can be performed by stirring for 1 hour to 1 day.

In another preferred example of this embodiment, the reactivity of the bis(2-chloroethyl)amine hydrochloride can be improved though heating. After mixing the bis(2-chloroethyl)amine hydrochloride and the base to obtain a mixture, the mixture can be heated for improving the reactivity of the bis(2-chloroethyl)amine hydrochloride. Then, the mixture of the bis(2-chloroethyl)amine hydrochloride and the base is cooled down, and $POCl_3$ is dropped into the mixture for performing the mentioned first stage reaction of this embodiment.

In one preferred example of this embodiment, $POCl_3$ can be reacted with 3-aminopropanol in the environment with the base to produce a second intermediate in the first stage reaction of the two-stage one-pot operation. Thereafter, bis(2-chloroethyl)amine hydrochloride is added into the result of the mentioned first stage reaction for performing the second stage reaction.

Additionally, in one preferred example of this embodiment, the mentioned solvent-free process for the preparation of cyclophosphamide can further comprise a step of adding catalyst. The mentioned catalyst can be selected from one of the following: N-hydroxysuccinimide (HOSu), hydroxybenzotriazole (HOBt), 4-Dimethylaminopyridine (DMAP). In one preferred example, the catalyst is added in the first stage of the two-stage one-pot operation. In one preferred example, the mentioned catalyst can be mixed with the phosphoryl chloride at the beginning.

There are several examples will be disclosed in the following for illustrating the solvent-free process for the preparation of cyclophosphamide according to this invention. However, this invention can also be applied extensively to other embodiments, and the scope of this present invention is expressly not limited except as specified in the accompanying claims.

EXAMPLE 1

Solvent-free Process for the Preparation of Cyclophosphamide

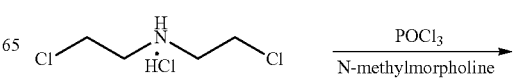

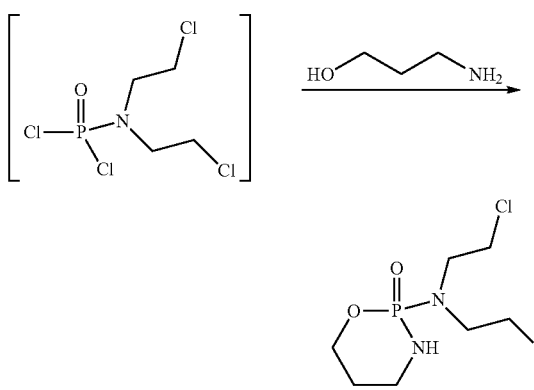

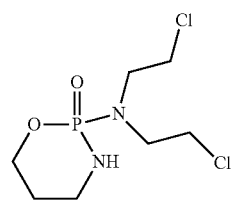

Bis(2-chloroethyl)amine hydrochloride (5 g, 0.028 mol) is put into a 100 mL two-necked flask, and N-methylmorpholine (8.4 eq) is added into the flask. After cooling the flask and the reactants therein to about 4° C., POCl$_3$ (4.3 g, 1.0 eq) is slowly dropped into the flask, and the mixture in the flask is stirred at room temperature for 5 hours. After that, the mixture in the flask is cooled to about 4° C., and 3-aminopropanol (2.1 g, 1.0 eq) is slowly dropped into the flask for 3 hours. After adding 3-aminopropanol into the flask, the mixture in the flask is stirred at room temperature for 15 hours. (The conversion yield of the solvent-free process of this specification can be determined with HPLC. In several repeat experiments, the conversion yield is about 62.4-77.6%.)

Subsequently, Ethyl acetate (40-70 mL) and H$_2$O (10 mL) are added into the flask. After well stirring, the mixture is separated into organic layer (ethyl acetate layer) and aqueous layer. The organic layer is taken out, and washed with 2N HCl$_{(aq)}$ (10 mL). After performing MTBE crystallization, white solid product is obtained (2.80-3.42 g, purity>99%). $^1$H-NMR (500 MHz, CD$_3$OD): δ=1.8-2.0 (m, 2H), 3.2-3.5 (m, 7H), 3.6-3.7 (m, 4H), 4.2-4.4 (m, 2H).

The purity of the white solid product is 99.84%, the purity is determined by high-performance liquid chromatography (HPLC). The HPLC analytic condition is as following: ODS-2 (5 μm, 4.6*250 mm) column as stationary phase and H$_2$O (0.2% NaH$_2$PO$_4$.H$_2$O)—MeCN (100:0 to 20:80, v/v, 0-25 min) as mobile phase; Flow rate: 1 ml/1 min.

EXAMPLE 2

Solvent-free Process for the Preparation of Cyclophosphamide with Catalyst

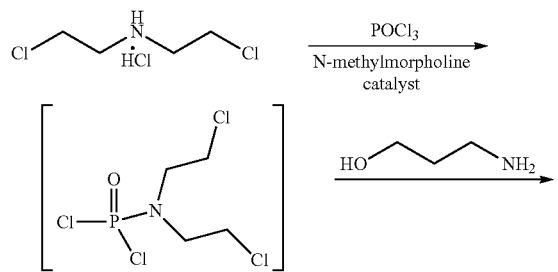

Bis(2-chloroethyl)amine hydrochloride (5 g, 0.028 mol), catalyst (0.05 eq), and N-methylmorpholine (8.4 eq) are placed into a flask. After cooling the flask and the mixture therein to about 4° C., POCl$_3$ (4.3 g, 1.0 eq) is slowly dropped into the flask. After adding POCl$_3$, the mixture in the flask is stirred at room temperature for 5 hours. After that, the mixture in the flask is cooled to about 4° C., and 3-aminopropanol (2.1 g, 1 eq) is slowly dropped into the flask for 3 hours. After adding 3-aminopropanol into the flask, the mixture in the flask is stirred at room temperature for 15 hours. (The conversion yield of repeat experiments determined with HPLC is about 60.8-73.0%.)

Subsequently, Ethyl acetate (70 mL) and H$_2$O (10 mL) are added into the flask. After well stirring, the mixture is separated into organic layer (ethyl acetate layer) and aqueous layer. The organic layer is taken out, and washed with 2N HCl$_{(aq)}$ (10 mL). After performing MTBE crystallization, white solid product is obtained (3.29 g, purity >99%). $^1$H-NMR (500 MHz, CD$_3$OD): δ=1.8-2.0 (m, 2H), 3.2-3.5 (m, 7H), 3.6-3.7 (m, 4H), 4.2-4.4 (m, 2H).

The results with different catalysts are as the following Table 1.

TABLE 1

| Entry | Base | Catalyst | Conversion yield |
|---|---|---|---|
| 1 | N-methylmorpholine | 0.05 eq DMAP | 60.8% |
| 2 | N-methylmorpholine | 0.05 eq HOSu | 73.0% |
| 3 | N-methylmorpholine | 0.05 eq HOBt | 61.9% |

EXAMPLE 3

Improving the Reactivity of bis(2-chloroethyl)amine Hydrochloride in Solvent-Free Process for the Preparation of Cyclophosphamide Bis(2-chloroethyl)amine hydrochloride (5 g, 0.028 mol), and N-methylmorpholine (8.4 eq) are placed into a flask. After heating the flask and the mixture therein to about 40° C. and keep for 1.5 hours to 1 day, the flask and the mixture therein are cooled to 4° C., and then POCl$_3$ (4.57 g, 1.06 eq) is slowly dropped into the flask. After adding POCl$_3$, the mixture in the flask is stirred at room temperature for 5 hours. After that, the mixture in the flask is cooled to about 4° C., and 3-aminopropanol (2.1 g, 1 eq) is slowly dropped into the flask for 3 hours. After adding 3-aminopropanol into the flask, the mixture in the flask is stirred at room temperature for 15 hours. The conversion yield determined with HPLC is about 69.8%.

EXAMPLE 4

Solvent-free Process for the Preparation of Cyclophosphamide

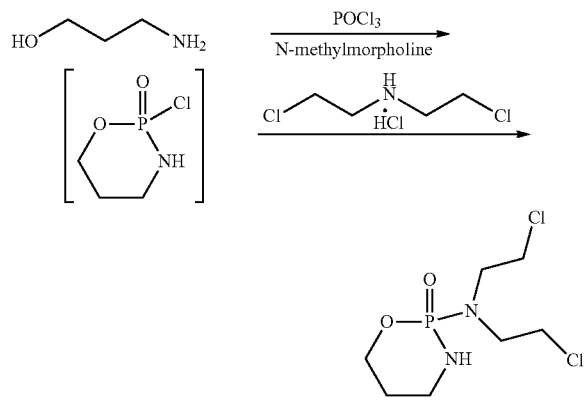

3-aminopropanol (2.1 g, 0.028 mol) and N-methylmorpholine (12.9 eq) are placed into a three-necked flask and stirred at room temperature. After cooling the mixture in the flask, $POCl_3$ (4.3 g, 0.028 mol) is slowly dropped into the mixture. After adding $POCl_3$, the mixture in the flask is stirred at room temperature for 15 hours. After that, bis(2-chloroethyl)amine hydrochloride] (5 g, 0.028 mol) is added into the mixture in the flask. The mixture in the flask is heated to about 40° C. and stirred for 6 hours. (The conversion yield determined with HPLC is about 10.0%.)

EXAMPLE 5

Solvent-free Process for the Preparation of Cyclophosphamide

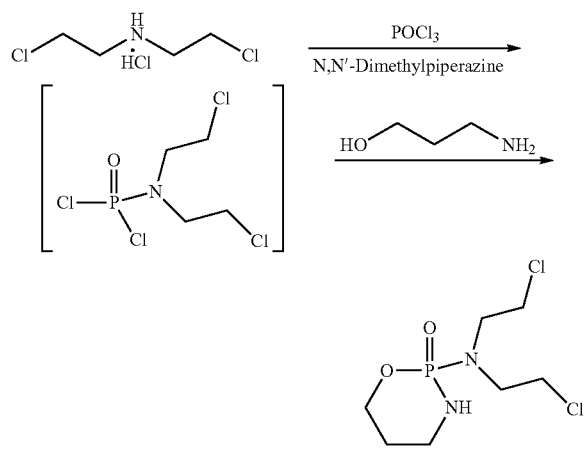

Bis(2-chloroethyl)amine hydrochloride (5 g, 0.028 mol) is put into a 100 mL two-necked flask, and N,N'-Dimethylpiperazine (7.1 eq) is added into the flask. After cooling the flask and the reactants therein to about 4° C., $POCl_3$ (4.49 g, 1.04 eq) is slowly dropped into the flask, and the mixture in the flask is stirred at room temperature for 5 hours. After that, the mixture in the flask is cooled to about 4° C., and 3-aminopropanol (2.1 g, 1.0 eq) is slowly dropped into the flask for 3 hours. After adding 3-aminopropanol into the flask, the mixture in the flask is stirred at room temperature for 15 hours. (The conversion yield determined with HPLC is about 11.84%.)

In general (organic) chemical reaction, the usage amount of solvent is about 10 to 20 times of the starting material(s). According to this invention, the disclosed preparation of cyclophosphamide is solvent-free, and the total volume of the mentioned preparation can be efficiently reduced because of "no solvent usage" in the reaction for preparing cyclophosphamide. For example, in a reaction of this invention, in one example of this invention, the usage amount of the starting material is 5 g, and the total volume of the reaction including other reagents is about 6 times of the starting material. The total volume of the reaction has been decreased more than 50% as comparing to a general chemical reaction. Therefore, the production capacity of the operation according to this invention can be 2 to 3 times of the production capacity of the operation in the prior art.

In summary, this application has reported a solvent-free process for the preparation of cyclophosphamide. The mentioned solvent-free process comprises reacting a phosphoryl halide, bis(2-chloroethyl)amine hydrohalide, 3-aminopropanol, and a base. The mentioned solvent-free process is a two-stage one-pot operation. There is no solvent used during the reaction for preparing cyclophosphamide. Comparing with the prior manufacturing processes of cyclophosphamide using solvents such as dichloromethane and dioxane during the reaction, the preparation of cyclophosphamide according to this invention does not use any solvent nor any dehydrate agent or pre-drying the reagents, so that the preparation of cyclophosphamide of this invention is more safety and is easier to be performed than the preparation in the prior art. Preferably, according to this invention, a green reaction without solvent used can efficiently improve the production capacity of each batch manufacturing process. Furthermore, for producing high potency drug such as cyclophosphamide, when improving the manufacturing process, the safety and health of operator(s) can be easily protected.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A solvent-free process for the preparation of cyclophosphamide, wherein the reaction step of the solvent-free process does not use solvent, comprising:
    reacting a phosphoryl chloride, a bis(2-chloroethyl)amine hydrochloride, a 3-aminopropanol, and a base, including the steps of:
        reacting one of said amines of said bis(2-chloroethyl) amine hydrochloride and 3-aminopropanol with phosphoryl chloride in the presence of said base to form an intermediate; and
        reacting said intermediate with another of said amines not used in the above step to form the cyclophosphamide,
    wherein said phosphoryl chloride, said bis(2-chloroethyl) amine hydrochloride, said 3-aminopropanol, said base, and said cyclophosphamide are represented as the following formula:

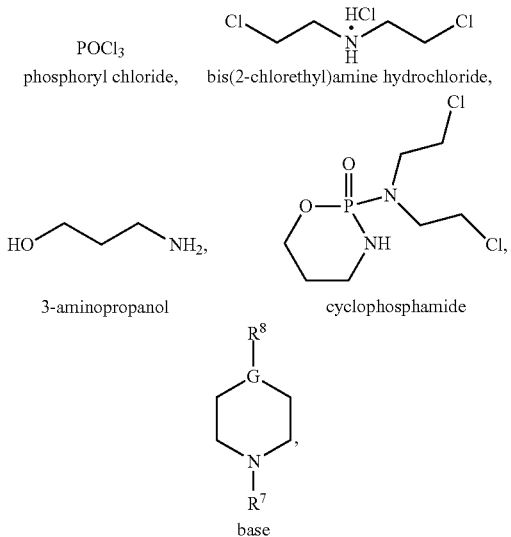

wherein G is selected from group consisting of the following: N, O, $R^7$ is selected from the group consisting of the following: C1-C3 straight-chain alkyl group, C1-C3 branched alkyl group, when G is N, $R^8$ is selected from the group consisting of the following: C1-C3 straight-chain alkyl group, C1-C3 branched alkyl group.

2. The solvent-free process for the preparation of cyclophosphamide according to claim 1, wherein the step of reacting said phosphoryl chloride, said bis(2-chloroethyl)amine hydrochloride, said 3-aminopropanol, and said base comprises:
reacting said phosphoryl chloride and said bis(2-chloroethyl)amine hydrochloride in the environment with said base to produce a first intermediate; and
reacting said first intermediate with said 3-aminopropanol to obtain the cyclophosphamide.

3. The solvent-free process for the preparation of cyclophosphamide according to claim 2, wherein said bis(2-chloroethyl)amine hydrochloride is mixed with said base to form a mixture, and the mixture is heated for increasing the reactivity of said bis(2-chloroethyl)amine hydrochloride before reacting with phosphoryl chloride.

4. The solvent-free process for the preparation of cyclophosphamide according to claim 2, wherein the step of reacting said phosphoryl chloride, said bis(2-chloroethyl)amine hydrochloride, said 3-aminopropanol, and said base is a two-stage one-pot operation, wherein the first intermediate is not isolated from the operation.

5. The solvent-free process for the preparation of cyclophosphamide according to claim 4, further comprising a step of adding a catalyst, wherein said catalyst is added in the first stage of the two-stage one-pot operation.

6. The solvent-free process for the preparation of cyclophosphamide according to claim 5, wherein said catalyst is selected from one or any combination of the group consisting of the following: N-hydroxysuccinimide (HOSu), hydroxybenzotriazole (HOBt), 4-Dimethylaminopyridine (DMAP).

7. The solvent-free process for the preparation of cyclophosphamide according to claim 1, wherein the step of reacting said phosphoryl chloride, said bis(2-chloroethyl)amine hydrochloride, said 3-aminopropanol, and said base comprises:
reacting said phosphoryl chloride and said 3-aminopropanol in the environment with said base to produce a second intermediate; and
reacting said second intermediate with said bis(2-chloroethyl)amine hydrochloride to obtain the cyclophosphamide.

8. The solvent-free process for the preparation of cyclophosphamide according to claim 7, wherein the step of reacting said phosphoryl chloride, said bis(2-chloroethyl)amine hydrochloride, said 3-aminopropanol, and said base is a two-stage one-pot operation, wherein the second intermediate is not isolated from the operation.

9. The solvent-free process for the preparation of cyclophosphamide according to claim 8, further comprising a step of adding a catalyst, wherein said catalyst is added in the first stage of the two-stage one-pot operation.

10. The solvent-free process for the preparation of cyclophosphamide according to claim 9, wherein said catalyst is selected from one or any combination of the group consisting of the following: N-hydroxysuccinimide (HOSu), hydroxybenzotriazole (HOBt), 4-Dimethylaminopyridine (DMAP).

* * * * *